United States Patent
Quadling et al.

(10) Patent No.: US 7,573,583 B2
(45) Date of Patent: *Aug. 11, 2009

(54) LASER DIGITIZER SYSTEM FOR DENTAL APPLICATIONS

(75) Inventors: Henley S. Quadling, Dallas, TX (US);
Mark S. Quadling, Plano, TX (US);
Alan Blair, St. Paul, MN (US)

(73) Assignee: D4D Technologies, LLC, Richardson, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/678,880

(22) Filed: Feb. 26, 2007

(65) Prior Publication Data

US 2007/0146726 A1 Jun. 28, 2007

Related U.S. Application Data

(63) Continuation of application No. 10/804,694, filed on Mar. 19, 2004, now Pat. No. 7,184,150.

(60) Provisional application No. 60/457,025, filed on Mar. 24, 2003.

(51) Int. Cl.
*G01B 11/30* (2006.01)
*G06K 9/00* (2006.01)
*A61C 5/00* (2006.01)
*A61B 6/00* (2006.01)
*A61B 5/103* (2006.01)
*A61B 5/117* (2006.01)

(52) U.S. Cl. .............. 356/602; 356/603; 356/608; 382/154; 433/215; 600/476; 600/590

(58) Field of Classification Search .............. None
See application file for complete search history.

(56) References Cited

U.S. PATENT DOCUMENTS

| | | | | |
|---|---|---|---|---|
| 4,575,805 A | * | 3/1986 | Moermann et al. | 700/163 |
| 5,424,836 A | * | 6/1995 | Weise et al. | 356/602 |
| 5,545,039 A | * | 8/1996 | Mushabac | 433/215 |
| 5,604,817 A | * | 2/1997 | Massen et al. | 382/120 |
| 5,702,249 A | * | 12/1997 | Cooper | 433/29 |
| 5,738,678 A | * | 4/1998 | Patel | 606/10 |
| 6,263,234 B1 | * | 7/2001 | Engelhardt et al. | 600/476 |
| 6,540,512 B1 | * | 4/2003 | Sachdeva et al. | 433/24 |
| 6,594,539 B1 | * | 7/2003 | Geng | 700/117 |
| 6,648,640 B2 | * | 11/2003 | Rubbert et al. | 433/24 |
| 6,674,893 B1 | * | 1/2004 | Abe et al. | 382/154 |
| 6,697,164 B1 | * | 2/2004 | Babayoff et al. | 356/609 |
| 6,977,732 B2 | * | 12/2005 | Chen et al. | 356/603 |
| 7,068,825 B2 | * | 6/2006 | Rubbert et al. | 382/128 |
| 7,184,150 B2 | * | 2/2007 | Quadling et al. | 356/602 |
| 7,215,430 B2 | * | 5/2007 | Kacyra et al. | 356/601 |

(Continued)

*Primary Examiner*—Gregory J Toatley, Jr.
*Assistant Examiner*—Gordon J Stock, Jr.
(74) *Attorney, Agent, or Firm*—Haynes and Boone LLP

(57) ABSTRACT

An intra-oral laser digitizer system provides a three-dimensional visual image of a real-world object such as a dental item through a laser digitization. The laser digitizer captures an image of the object by scanning multiple portions of the object in an exposure period. The intra-oral digitizer may be inserted into an oral cavity (in vivo) to capture an image of a dental item such as a tooth, multiple teeth or dentition. The captured image is processed to generate the three-dimension visual image.

14 Claims, 15 Drawing Sheets

U.S. PATENT DOCUMENTS

| | | | |
|---|---|---|---|
| 7,259,871 B2 * | 8/2007 | Chen | 356/603 |
| 7,312,924 B2 * | 12/2007 | Trissel | 359/497 |
| 7,342,668 B2 * | 3/2008 | Quadling et al. | 356/603 |
| 7,385,708 B2 * | 6/2008 | Ackerman et al. | 356/603 |
| 7,494,338 B2 * | 2/2009 | Durbin et al. | 433/29 |
| 2003/0045798 A1 * | 3/2003 | Hular et al. | 600/476 |
| 2003/0164952 A1 * | 9/2003 | Deichmann et al. | 356/603 |

* cited by examiner

LASER DIGITIZER SYSTEM FOR DENTAL APPLICATIONS

PRIORITY AND CROSS REFERENCE TO RELATED APPLICATION

This application is a continuation of Ser. No. 10/804,694, filed Mar. 19, 2004.

BACKGROUND OF THE INVENTION

1. Related Field

The invention relates to three-dimensional imaging of physical objects. In particular, the invention relates to intra-oral (in vivo) laser imaging of dental items including dentition, prepared dentition, impression materials and the like.

2. Description of the Related Art

A three-dimensional ("3D") visual image of a physical object may be generated by a computer that processes data representing shapes, surfaces, contours and/or characteristics of the object. The data is generated by optically scanning the object and detecting or capturing the light reflected from the object. Principles such as Moir, interferometry, and laser triangulation, may be used to model the shape, surfaces, contours and/or characteristics of the object. The computer displays the 3D image on a screen, or computer monitor.

Existing intra-oral 3D imaging systems use a variation of the Moire imaging technique. Such systems use structured white light to project a two-dimensional ("2D") depiction on the object to be imaged. Moir systems use the 2D lateral information, and input from skilled operators, to determine relative dimensions of adjacent features. Moire systems also use a sinusoidal intensity pattern that is observed from a position other than a projection angle that does not appear sinusoidal. Therefore, an inferred point-by-point phase angle between an observed and a projected image may be correlated to height data.

Intra-oral dental imaging systems, based on the Moiré technique image a dental item, such as a tooth, directly from or below occlusal surfaces of the tooth. Such systems have low depth resolution and may not accurately image or represent a surface that is undercut or shadowed. Intra-oral dental imaging systems also may require a powder or the like to provide a uniform color and reflectivity required by limitations of the white light techniques. The powder layer may increase or introduce errors in the digitized data, due to non-uniformity of the powder thickness.

BRIEF SUMMARY OF THE INVENTION

The embodiments provide a laser imaging system that generates a three-dimensional image of a scanned physical object such as a dental item. An embodiment includes intra-oral laser imaging systems, methods, apparatuses, and techniques that provide digitization of a physical object to generate a 3D visual image of the object. An intra-oral digitizer generates a laser pattern that may be projected on or towards a dental item, dentition, prepared dentition, or impression material in an oral cavity (in vivo). The intra-oral digitizer may include a projection optics system that remotely generates the laser pattern and relays that pattern so that it may be projected on or towards a dental item or items in vivo. The intra-oral digitizer also includes an imaging optical system that detects or captures light reflected from the dental item. The imaging optical system, or a portion thereof, may be inserted in the oral cavity at a known angle with respect to the projection system to capture light reflected from the dentition.

The captured light may be used to generate data representative of the 3D image of the dentition. The 3D visual image may be displayed on a computer monitor, screen, display, or the like. The data also may be used to form a dental restoration using known techniques such as milling techniques. The restoration may be a crown, bridge, inlay, onlay, implant or the like.

The intra-oral laser digitizer may have a light source, a focusing objective, a two-axis scanner, an optical relay system, an image optics system, and a processor configured to carry out instructions based on code, and process digital data. The light source may have a laser LED and collimating optics producing a collimated beam of light that is projected to the two-axis scanner. The scanner redirects, or scans, the collimated beam of light through at least two axes at high speeds. The scanner may scan the beam at a selected constant frequency or a variable frequency and duty cycle. The scanned beam is projected toward the optical relay system, which focuses the beam as a dot on the surface of the object.

The optical relay system may include focusing lenses, relay lenses and a prism, through which the scanned beam may be projected. The optical relay system focuses the desired pattern of the laser dot generated by the scanner on the object. The laser dot may be focused so that the dot traverses a curvilinear segment across the object. The optical relay system may include one or more optical components such as standard optical glass lenses, or gradient index glass lenses.

The image capture instrument detects the light reflected from the object through a relay optics system. The image capture system generates data representing a captured image of the scanned beam. The image capture system may be configured to capture images of one or more scanned curvilinear segments during an exposure period. The computer processes the data to generate the three-dimensional visual image of the object on a computer monitor, a screen, or other display.

Multiple images of the object may be recorded and processed by the computer to produce a 3D map of the object. The multiple images can be captured from multiple positions and orientations with respect to the object. The individual images are merged to create an overall 3D map of the object. The images may be captured and processed to provide a real time image of the surface of the object. The real time image may provide an instant feedback mechanism to an operator of the system. The digitizer system may include software that displays the overall 3D image captured in real time. The software also may include feedback and identification provided to the operator of suggested viewpoints to complete the overall 3D image. The software also may identify crucial features in the scanned data set during a data acquisition process. These features include margins and neighboring dentition. This software also may display highlighted features or possible problem areas, as the operator captures additional viewpoints.

A one- or two-axis tilt sensor may determine a relative angle between images. The imaging system may also be used as a standard 2D dental camera through the addition of a background light source.

Control, acquisition, and interaction may be initiated via foot controls, controls on the intra-oral device, or by voice recognition of spoken commands, or like methods.

An embodiment quickly and accurately digitizes 3D surfaces of an object, such as prepared teeth and impression materials including bite registration strips. The intra-oral digitizer also provides improved imaging abilities over prior art intra-oral dental imaging systems. The digitizer also simplifies operator requirements and interactions for an intra-oral dental scanning system.

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DESCRIPTION OF THE EMBODIMENTS OF THE INVENTION

Figure 1:
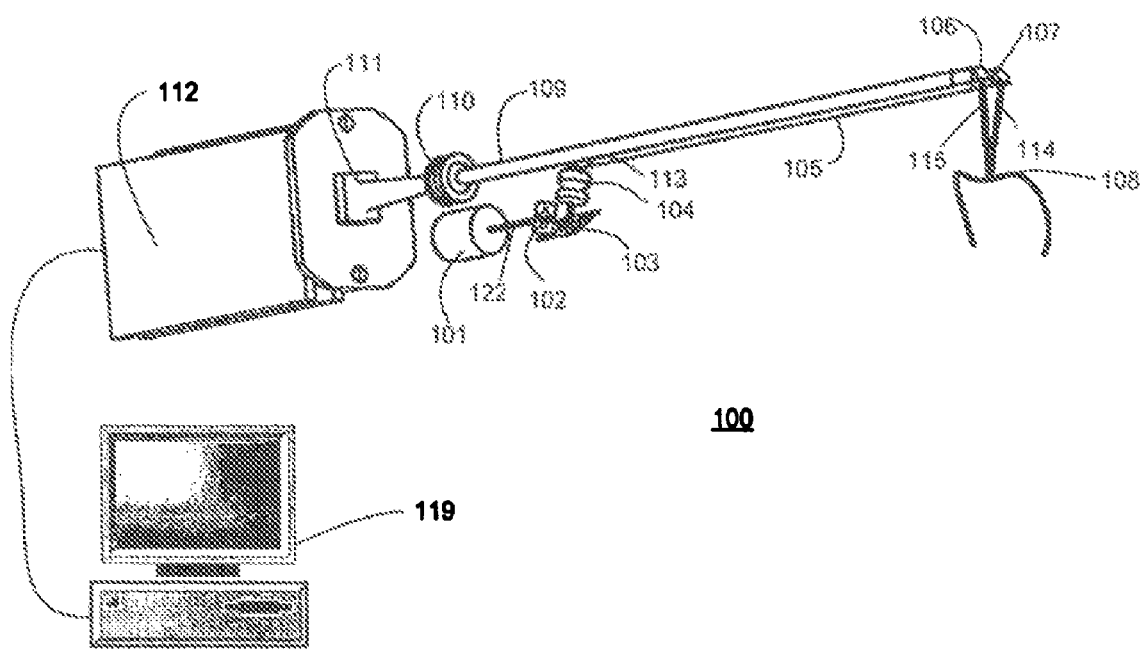
FIG. 1 illustrates an intra-oral laser digitizer coupled to a processor.

FIG. 1 illustrates an example of an intra-oral laser digitizer 100. FIGS. 2-5 illustrate various views of the intra-oral laser digitizer 100 of FIG. 1. The intra-oral digitizer 100 generates a 3D image of an object 108 such as a dental item. The intra-oral digitizer 100 generates a laser pattern that may be projected on or towards a dental item, dentition, or prepared dentition in an oral cavity (in vivo). The intra-oral digitizer 100 may remotely generate the laser pattern and relay the pattern towards the dental item or items in vivo. The laser pattern may be relayed through relay optics such as prisms, lenses, relay rods, fiber optic cable, fiber optic bundles, or the like. The intra-oral digitizer 100 also may detect or capture light reflected from the dental item in vivo. The intra-oral digitizer 100, or a portion thereof, may be inserted in the oral cavity to project the laser pattern and to detect the reflected laser pattern from the dental item or items in the oral cavity. The captured light may be used to generate data representative of the 3D image of the dentition. The data may be used to display the 3D image. The data also may be used to form a model of the object using known techniques such as milling techniques. The model of the object may be a dental restoration such as a crown, bridge, inlay, onlay, implant or the like. The data also may be used for diagnostic purposes.

The laser digitizer 100 includes a laser light source 101, a first scanner 102 (x scanner), a second scanner 103 (y scanner), a lens assembly 104, a first reflecting prism 113, a first optics relay 105, a second reflecting prism 107, a third reflecting prism 106, a second optics relay 109, imaging optics assembly 110, imaging sensor 111, and an electronic circuit 112. The intra-oral laser digitizer 100 may be coupled to a processor 119.

The laser light source 101 may include collimating optics (not shown) that generate a laser beam of light 122 from the light source 101. The collimated light beam 122 is characterized by parallel rays of laser light. The laser beam 122 is projected to the first scanner 102.

The laser light source 101 may include a laser diode or LED that generates a laser light beam having an elliptical-shaped cross-section. The collimating optics may be configured to circularize the elliptical beam and to generate a circular spot. The circular spot may be used to scan a uniform line across the surface of the object 108. The laser diode may be any commercially available laser diode configured to emit a laser light beam, such as the Blue Sky Research Mini-Laser 30 mWatt laser with 0.6 mm collimated beam, model number Mini-635D3D01-0.

The laser light source 101 also may modulate the laser light beam. The laser light source 101 may be coupled to a modulator that adjusts or interrupts light flow from the source at high modulation or switching rate. The modulation may be in the range of substantially 1 kHz to substantially 20 MHz. A scan pattern may be generated on the object, by modulating the laser light source 101.

The first scanner 102 includes an x-scanner mirror having a substantially flat reflecting surface. The reflecting surface of the x-scanner mirror, may be rectangular-shaped having dimensions approximately 1.5 mm by approximately 0.75 mm. The laser beam 122 from the light source 101 may have a width no greater than the smallest dimension of the first scanner 102. For example, the width of the laser beam may be approximately 0.6 mm. The beam of light 122 from the laser light source 101 is incident upon the reflecting surface of the first scanner 102.

The second scanner 103 includes a y-scanner mirror having a substantially flat reflecting surface. The reflecting surface of the y-scanner mirror, may be rectangular-shaped having dimensions approximately 1.5 mm by approximately 0.75 mm. The reflecting surfaces of the x-scanner and the y-scanner may be mirrors or the like.

Figure 2:
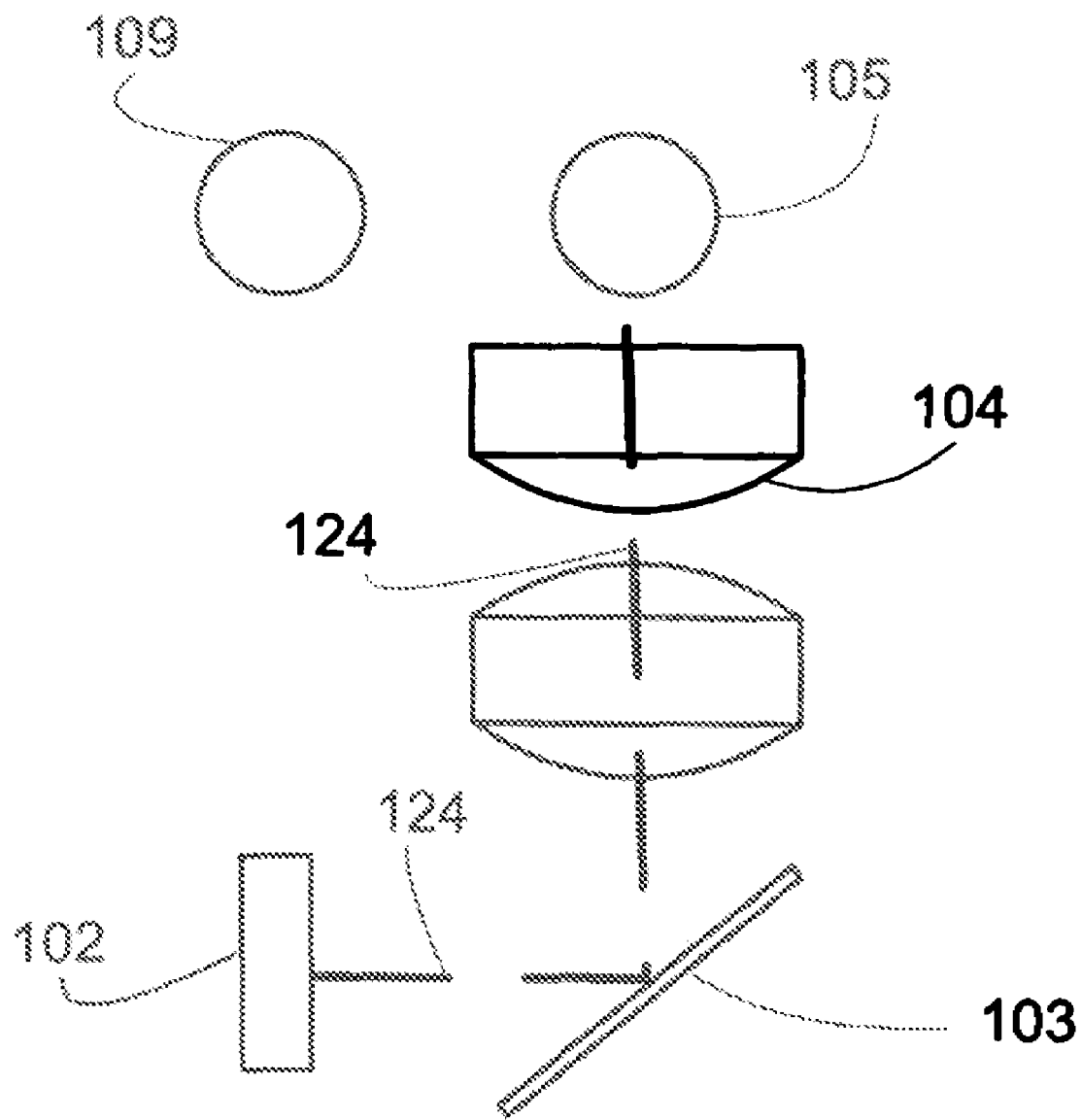
FIG. 2 illustrates a front view of a portion of the intra-oral laser digitizer of FIG. 1.

FIG. 2 illustrates the second scanner 103 positioned substantially orthogonal to the first scanner 102. The first scanner 102 directs the beam of light 122 towards the second scanner 103. The beam 122 directed from the first scanner 102 is incident upon the reflecting surface of the second scanner 103. The first scanner 102 directs the beam 122 along an arc onto the reflecting surface of the second scanner 103. The reflective surface of the first scanner 102 may be rotated through an axis of rotation to create the arc on the reflective surface of the second scanner 103. Together, the reflecting surfaces of the first scanner 102 and the second scanner 103 form a two-axis scanner assembly 116. The reflective surface of the second scanner 103 rotates through the y-axis to direct a two-axis scanned beam 124 in an orthogonal direction.

The scanned beam 124 is incident upon the lens assembly 104. The lens assembly 104 focuses the scanned beam 124 through the first reflecting prism 113. The first reflecting prism 113 directs a scanned image 125 to the first optics relay 105.

Figure 3:
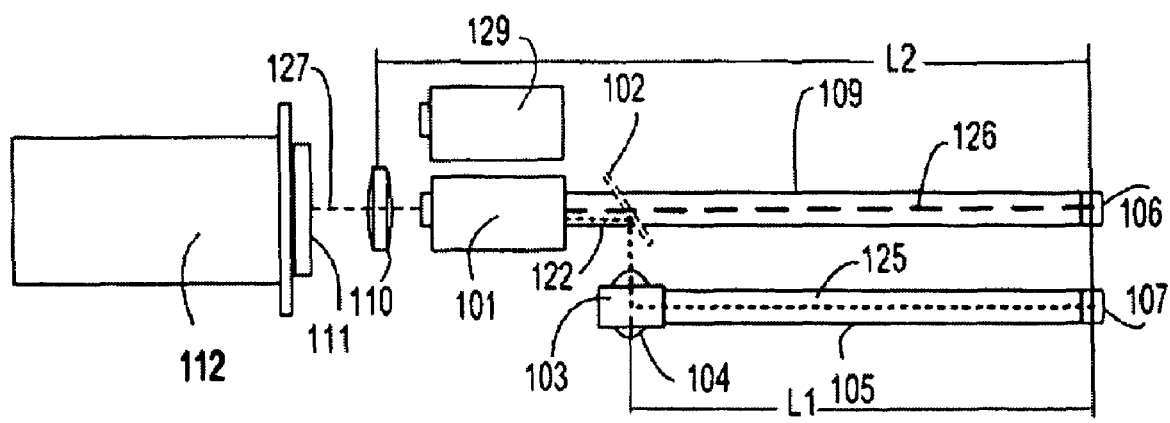
FIG. 3 illustrates a top view of the intra-oral laser digitizer of FIG. 1.

FIG. 3 illustrates the first optics relay 105 relaying the scanned image 125 to the second reflecting prism 107. The second reflecting prism 107 may be inserted into an oral cavity to project the laser pattern toward one or more dental items to be imaged. The first optics relay 105 transmits the laser pattern generated by the light source 101, the first and second scanner 102, 103 and the lens assembly 104 to a remote location, such as an oral cavity. The second reflecting prism 107 projects a scanned beam 114 towards the object 108 so that a light pattern may be projected on the object 108. The first optics relay 105 may be any commercially available relay optics system. The first optics relay 105 may be a relay lens such as a GRIN lens, a fiber optic cable, a fiber optic bundle, or similar device for relaying an optical image over a distance L1. An example of a first optics relay 105 is a Grin-Tech rod lens with part number 12534082-4C-9 attached to the GrinTech objective grin lens with part number CR1032-2.

Figure 4:
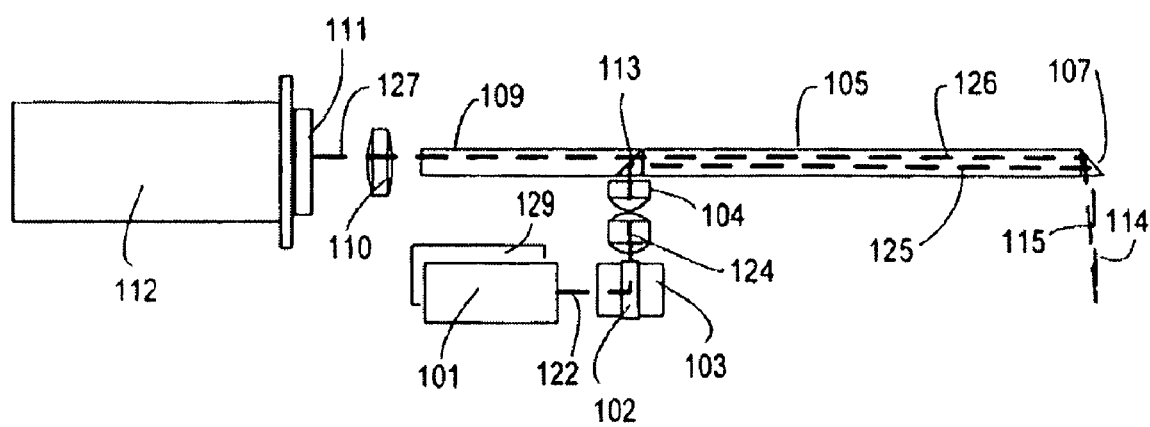
FIG. 4 illustrates a side view the intra-oral laser digitizer of FIG. 1.

As shown in FIG. 4, a reflection 115 of the scanned beam 114 from the surface of the object 108 is captured through the third reflecting prism 106 to relay captured reflection 126. The third reflecting prism 106 may be inserted into an oral cavity to detect or capture reflections of the laser pattern from the one or more dental items to be imaged. The second optics relay 109 transmits captured reflection 126 for a distance L2 from the oral cavity to the imaging optics assembly 110. The captured reflection 126 from the object 108 is imaged and focused by the imaging optics 110 to provide a focused beam 127. The focused beam 127 is projected towards the imaging sensor 111. The imaging sensor 111 may be a CCD sensor, a CMOS sensor, or other light sensitive device or array of light sensitive devices. The second optics relay 109 may be any commercially available relay optics system. The second optics relay 109 may be a relay lens such as a GRIN lens, a fiber optic cable, a fiber optic bundle, or similar device for relaying an optical image over a distance L2. An example of the second optics relay 109 is the GrinTech rod lens with part number 12534082-4C attached to the GrinTech objective grin lens with part number CR1032-2.

The imaging sensor 111 may be coupled with electrical circuit 112. The electrical circuit 112 may include electrical and electronic components suitable for processing electrical signals of the intra-oral digitizer 100. The electrical circuit 112 may be located or enclosed within a suitable enclosure. The enclosure may be a hand-held enclosure or have a form factor suitable for being handheld, for enclosing the electrical circuit 112 and for manipulating the intra-oral digitizer 100 in vivo. The enclosure and electrical circuit may be remotely located from the second and third reflecting prisms 107, 106. The electrical circuit 112 may modulate the light source 101, and drive the scanning mirrors 102 and 103. The electrical circuit also may gather electronic data received from the imaging sensor 111. The electrical circuit also may perform additional processing and communication with an external processor 119 via a cable or wireless or some other communications link.

Figure 5:
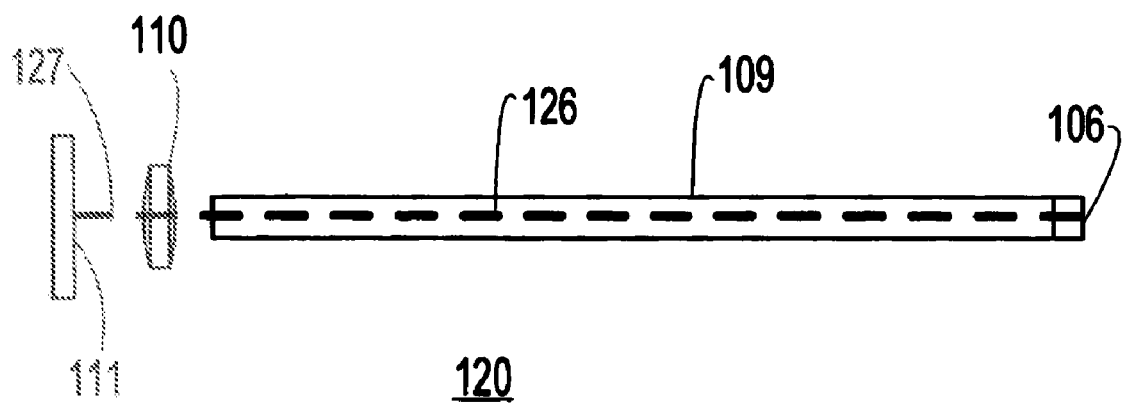
FIG. 5 illustrates an imaging optical system of the intra-oral laser digitizer of FIG. 1.

FIG. 5 illustrates an imaging optics system 120 of the laser digitizer 100. The imaging optics system 120 may include the third reflecting prism 106, the second optics relay 109, the imaging optics 110 and the imaging sensor 111. The imaging optics system 120 generates a digital signal representative of the capturer reflection 126.

Figure 6:
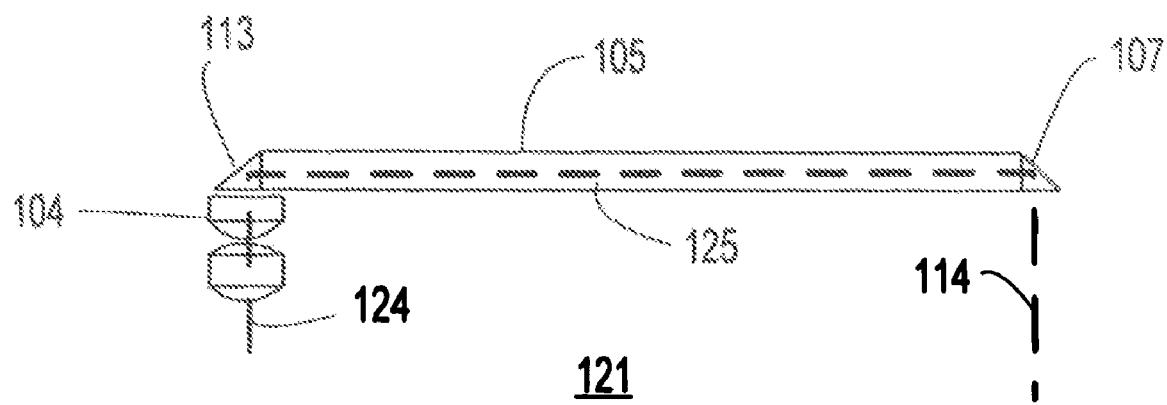
FIG. 6 illustrates a projection optics system of the intra-oral laser digitizer of FIG. 1.

FIG. 6 illustrates the projection optics system 121, including the lens assembly 104, the first reflecting prism 113, the first optics relay 105, and the second reflecting prism 107. The projection optics system 121 may project the scanned image in the direction of the object 108 so as to project the laser pattern in vivo.

Figure 7:
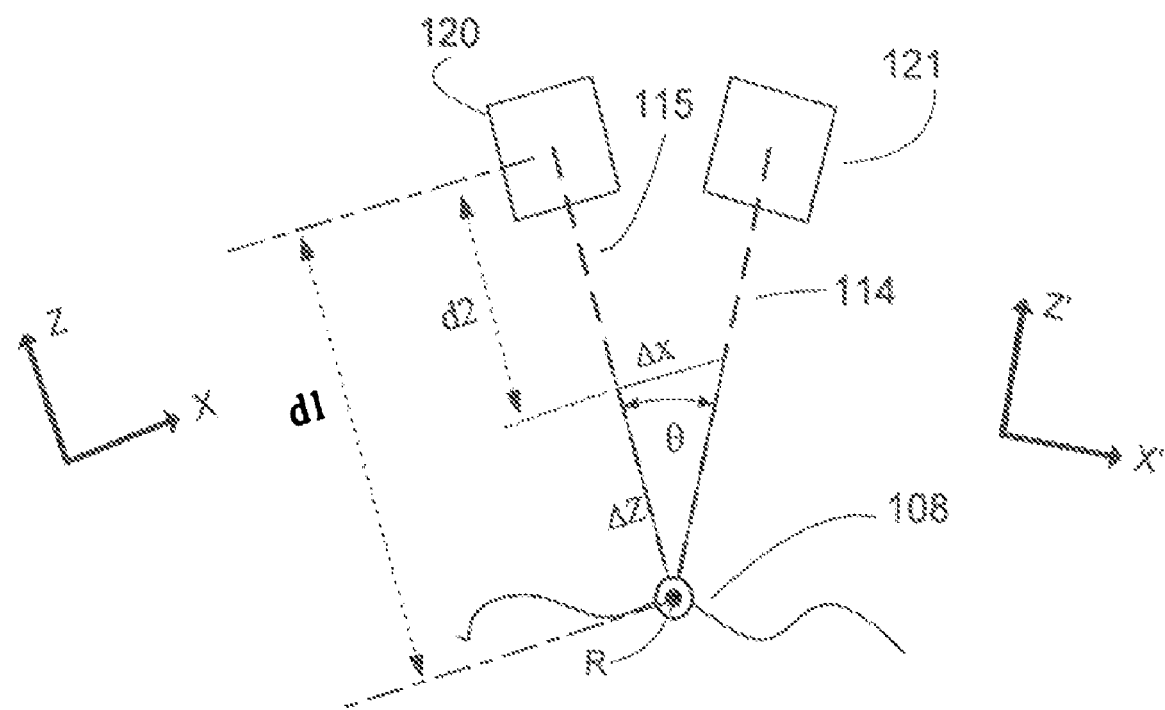
FIG. 7 illustrates a projection of a laser light beam on an object.
Figure 8:
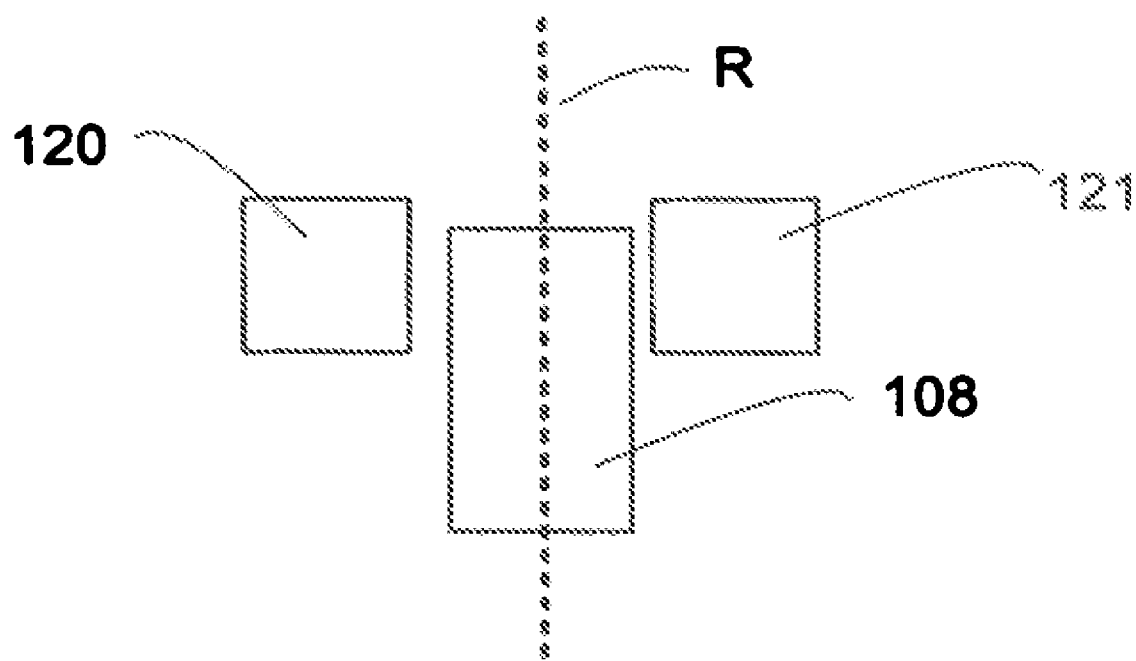
FIG. 8 illustrates a top view of a projection of a laser light beam.

FIG. 7 illustrates a front view of a portion of the intra-oral laser digitizer 100. The scanned beam 114 is directed from the projection optics system 121 in the direction of the object 108. Reflected light 115 is captured or detected by the imaging optics system 120. The imaging optics system 120 may be characterized by a coordinate system having axes X, Y, Z and the projection optics system 121 may be characterized by a coordinate system having axes X'Y'Z'. The Z' axis projects vertically from a center of the second reflecting prism 107 to the object 108, and Z is the axis projected vertically from the surface of the object at 108 to a center of the third reflecting prism 108. The X' axis is orthogonal to the Z' axis and in a horizontal plane with respect to the front of the intra-oral device 100. The X axis is orthogonal to the Z axis. The Y' axis may be defined according to the X' axis and the Z' axis in a right-handed coordinate system, as illustrated in the top view of the second reflecting prism 106 and the third reflecting prism 107, as illustrated in FIG. 8. The Y axis may be defined according to the X' axis and the Z' axis in a right-handed coordinate system, as illustrated in the top view of the second reflecting prism 106 and the third reflecting prism 107, as illustrated in FIG. 8.

An angle between the Z axis and Z' axis may be designated as θ. A distance from a center of the third reflecting prism 106 to the point on the object 108 may be referred to as d1 and a distance from the center of the third reflecting prism 106 to a top of a depth of focus region may be referred to as d2.

Figure 9:
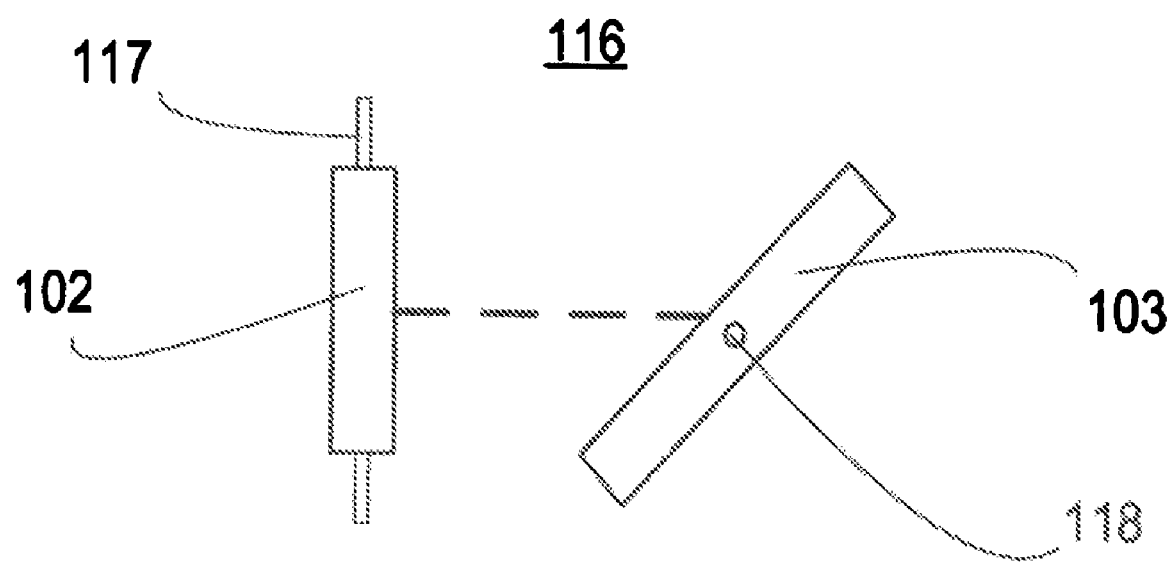
FIG. 9 illustrates a two-axis scanner of the intra-oral laser digitizer of FIG. 1.

FIG. 9 illustrates a two-axis scanner assembly 116. The two-axis scanner assembly may include the first scanner 102 and the second scanner 103. The first scanner 102 includes a reflective surface that rotates about axis 117. The reflective surface of the first scanner 102 directs the light to the reflecting surface of the second scanner 103. The reflective surface of the second scanner 103 rotates about the axis 118.

The reflective surfaces of the scanners 102 and 103 may be rotatably coupled with a respective motor, other electromagnetic driving mechanism, or electrostatic driving mechanism such as magnets, coils or other electromagnetic coupling that control a rotational movement of the corresponding reflective surface to effect the scanning of the collimated light beam.

The two-axis scanner 116 redirects, or scans, the collimated light beam to form a scanned light beam 114 having a position that varies over time. The scanned beam 114 is directed by the two-axis scanner 116 to the lens assembly 104 and the first optics relay 105. The two-axis scanner 116 redirects the collimated light beam in at least two or more axes 117, 118 where each axis is substantially perpendicular to the axis of the collimated light beam. The first and second scanners 102, 103 may have essentially perpendicular axes, and may be essentially orthogonal with respect to each other. The scanners 102, 103 also may be positioned at an arbitrary angle relative to each other.

Additional scanners also may be included to scan the collimated light beam. The scanners 102, 103 may be positioned orthogonally so that the collimated laser beam incident on the reflectors may be scanned or redirected in at least two axes. The first scanner 102 scans the beam along one axis, such as an x-axis. The second scanner 103 may be positioned so that the beam along the x-axis incident upon the second scanner 103 may be scanned along an orthogonal direction to the x-axis, such as a y-axis. For example, the first and second scanner 102, 103 may be positioned orthogonal with respect to each other so that the first scanner 102 scans the beam along the x-axis and the second scanner 103 scans the beam along an orthogonal direction to the x-axis, such as a y-axis.

The first scanner 102 also may have a spinning polygon mirror such that the rotatable second reflector 103 and the spinning polygon reflector 102 together also are configured to scan the laser beam in two axes. The spinning polygon mirror 102 may scan the collimated light beam along an x-axis and the rotatable mirror 103 may scan the collimated light beam along a y-axis. Each axis, the x-axis and y-axis, may be substantially orthogonal with one another to generate a scanned light beam along two substantially orthogonal axes.

The two-axis scanner 116 also may include a single reflecting surface that scans a beam of light along two axes. The reflecting surface may be driven electromagnetically or electrostatically to rotate the reflecting surface about two essentially orthogonal axes individually or simultaneously.

The two-axis scanner 116 may be include one or more Microelectro-mechanical systems ("MEMS"), which have reflecting surfaces that may be driven electromagnetically or electrostatically or using a piezo crystal or otherwise mechanically to rotate the reflecting surface about two essentially orthogonal axes individually or simultaneously.

The two-axis scanner 116 also may include a programmable position controller. The position controller may be a component of the two-axis scanner 116 or may be incorporated with the electronic circuit 112. The controller may control movement of the scanners 102, 103 by providing control signals to the drive mechanisms of the reflective surfaces of the scanners 102, 103. The controller controls the movement of the scanners 102, 103 so that the collimated laser beam is redirected to provide to a scan sequence. The coordinate system for the two-axis scanner 116 is referred to as X'Y'Z'.

As shown in FIGS. 7 and 8, the object 108 to be imaged is positioned within a field of view of projection optics 121 and the imaging optics system 120. The projection optics 121 is positioned at the angle θ with respect to an optical axis of the imaging optics system 120 so that when the focused dot is scanned across the surface of the object 108 the light is reflected towards the imaging optics system 120 at angle θ. The two-axis scanner 116 moves the scanned beam 114 so that the focus point of the laser dot from the projection optics 121 traverses through a pattern across the surface of the object 108.

The imaging optics system 120 may be configured and/or positioned to have a field of view that includes the focused laser dot projected on the object 108. The imaging optics system 120 detects the laser dot as it is scanned across the surface of the object 108. The imaging optics system 120 includes an image sensor 111 that is sensitive to the light reflected from the object 108. The imaging optics system 120 may include an imaging lens 110 and an image sensor 111 and the second optics relay 109 and a prism or fold mirror 106. The imaging lens 110 is configured to focus the light reflected from the object 108 towards the image sensor 111. Based on a light detected from the object 108, the image sensor 111 generates an electrical signal representative of the surface characteristics (e.g., the contours, shape, arrangement, composition, etc.) of the object 108.

The image sensor 111 captures an image of the scanned surface of the object 108. The image sensor 111 may be a photo-sensitive or light sensitive device or electronic circuit capable of generating signal representative of intensity of a light detected. The image sensor 111 may include an array of photodetectors. The array of photodetectors may be a charge coupled device ("CCD") or a CMOS imaging device, or other array of light sensitive sensors capable of generating an electronic signal representative of a detected intensity of the light. The image sensor 111 may comprise a commercially available CCD or CMOS high resolution video camera having imaging optics, with exposure, gain and shutter control, such as the Silicon Imaging USB Camera SI-1280F-U.

Each photo-detector of the image sensor 111 generates an electric signal based on an intensity of the light incident or detected by the photo-detector. In particular, when light is incident to the photo-detector, the photo-detector generates an electrical signal corresponding to the intensity of the light. The array of photo-detectors includes multiple photo-detectors arranged so that each photo-detector represents a picture element, or pixel of a captured image. Each pixel may have a discrete position within the array. The image capture instrument 120 may have a local coordinate system, XY such that each pixel of the scanned pattern corresponds to a unique coordinate (x,y). The array may be arranged according to columns and rows of pixels or any other known arrangement. By virtue of position of the pixel in the array, a position in the image plane may be determined. The imaging optics system 120 converts the intensity sensed by each pixel in the image plane into electric signals that represent the image intensity and distribution in an image plane.

The CMOS image sensor may be configured to have an array of light sensitive pixels. Each pixel minimizes any blooming effect such that a signal received by a pixel does not bleed into adjacent pixels when the intensity of the light is too high.

The two-axis scanner 116 may be configured to scan the laser beam 114 across the surface of the object 108 via the projection optics 121 in various patterns. The pattern may cover a portion of the surface of the object 108 during a single exposure period. The pattern also may include one or more curves or any known pattern from which the characteristics, elevations and configurations of the surface of the object 108 may be obtained.

During an exposure period, an image of a portion of the surface of the object is captured. The beam 114 scans the object 108 via the two-axis scanner 116 and the projection optics 121 in a selected pattern, allowing the imaging sensor 111 to detect the light reflected from object 108. The image sensor 111 generates data representative of the surface characteristics, contours, elevations and configurations of the scanned portion or captured image. The data representation may be stored in an internal or external device such as a memory.

Figure 10:
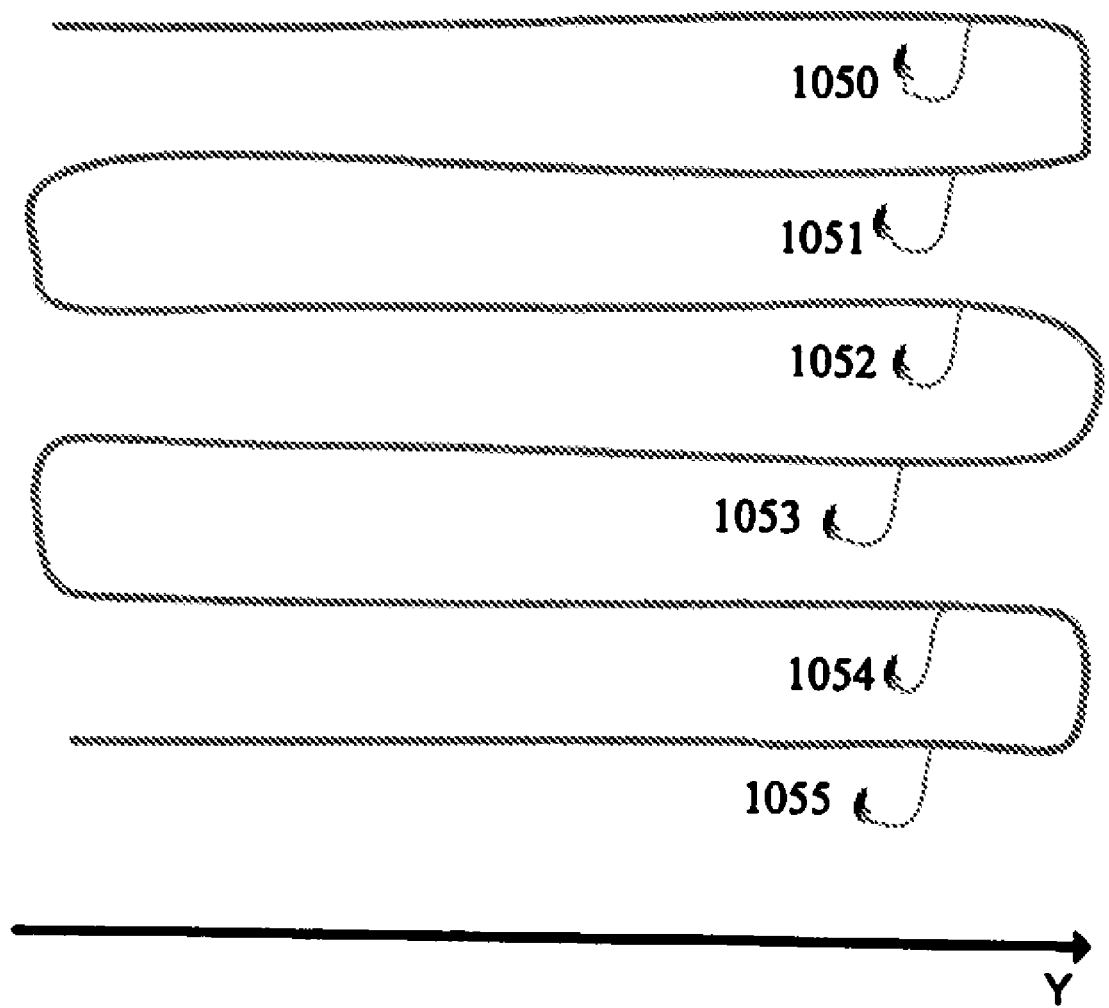
FIG. 10 illustrates an image of a light pattern of the intra-oral digitizer, as projected on and viewed from a flat surface.

FIG. 10 illustrates an example of a scanned pattern of light 1048 as viewed from a substantially flat surface. The scanned pattern 1048 may include multiple curves 1050-1055 that are generated by the scanner 116. A portion of the curves 1050-1051 may be essentially parallel to each other. The curves 1050-1055 also may represent or include a connected series of points or curvilinear segments where a tangent vector n at any single point or segment obeys the following rule:

$$|n \cdot R| \neq 0 \qquad (1)$$

where R is a triangulation axis that is substantially parallel to Y and Y' and passes through an intersection of an axial ray from the third reflecting prism 106 of the image optics system 120 and an axial ray from the second reflecting prism 107 of the optical projection system 121. Accordingly, the angle between the tangent n at any point or segment of the curve and the triangulation axis R is not 90 degrees. Each curve 1050-1055 also may have a cross-sectional intensity characterized by a function that may have a sinusoidal variation, a Gaussian profile, or any other known function for cross-sectional intensity. In an embodiment, a minimum angle between a valid ray between the second reflecting prism 107 relative to a valid axial ray of the third reflecting prism 106 is non-zero.

During a subsequent scan period, the beam 114 is scanned in a pattern across an adjacent portion of the object 108 and an image of the adjacent portion is captured. The scanned beam 114 may scan a different area of the surface of the object 108 during subsequent exposure periods. After several exposure periods in which the beam 114 is scanned across the various portions of the object 108 and images of those scanned portions captured, a substantial portion of the object may be captured.

The processor 119 may be coupled to the imaging optics system 120 and configured to receive the signals generated by the image capture instrument 120 that represent images of the scanned pattern on the object 108. The processor 119 may process and display the signals generated by the image optics system 120. The processor 119 also may be coupled to the laser light source and control selected or programmed applications of the laser light. The processor 119 also may be coupled with the two-axis scanner 116 and programmed to control the scanning of the collimated light The image optics system 120 may be characterized by a local coordinate system X, Y, Z, where the X and Y coordinates may be defined by the image imaging optics system 120. A value for the Z coordinate may be based on the distance $d_1$ and $d_2$ so that $d_1 \leq z \leq d_2$. A point from a projected curve incident to a plane perpendicular to Z will appear to be displaced in the X direction by $\Delta x$. Based on a triangulation angle, the following condition may exist:

$$\Delta z = \frac{\Delta x}{\text{Tan}\theta} \tag{2}$$

For a given curve (e.g. curve 1050) in the projection pattern there may be unique relations $\theta(y)$, $z_{base}(y)$ and $x_{base}(y)$. The relations $\theta(y)$, $z_{base}(y)$ and $x_{base}(y)$ relations may be determined through calibration. The calibration may be performed for example by observing the curve 1050 as projected on a plane surface. The plane surface may be perpendicular to the imaging optics system 120 at two or more distances d along the Z axis from the image optics system 120. For each y value along the curve 1050, using at least two such curves with known z values of $z_1$ and $z_2$, where $z_1 < z_2$, $\Delta z$ may be computed as $\Delta z = z_2 - z_1$. A value $\Delta x$ may be observed using imaging optics system 120. Using equation (2), $\theta(y)$ may be computed. The corresponding value $z_{base}(y)$ may be set equal to $z_1$. The corresponding value $x_{base}(y)$ may be equal to an x value at the point y on the curve corresponding to $z_1$. Additional curves may be used to improve accuracy of through averaging or interpolation.

Figure 11:
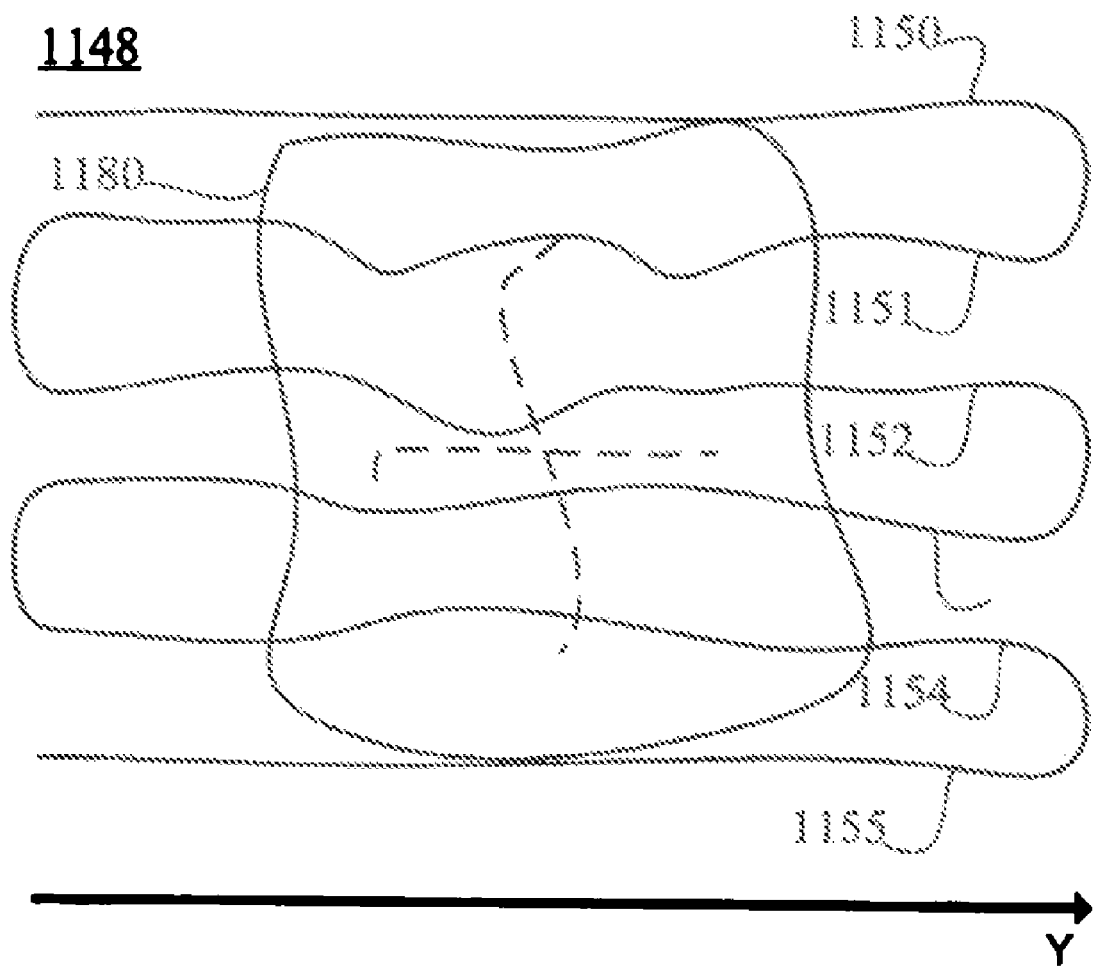
FIG. 11 illustrates the light pattern of FIG. 10 as projected on an object to be imaged.
Figure 12:
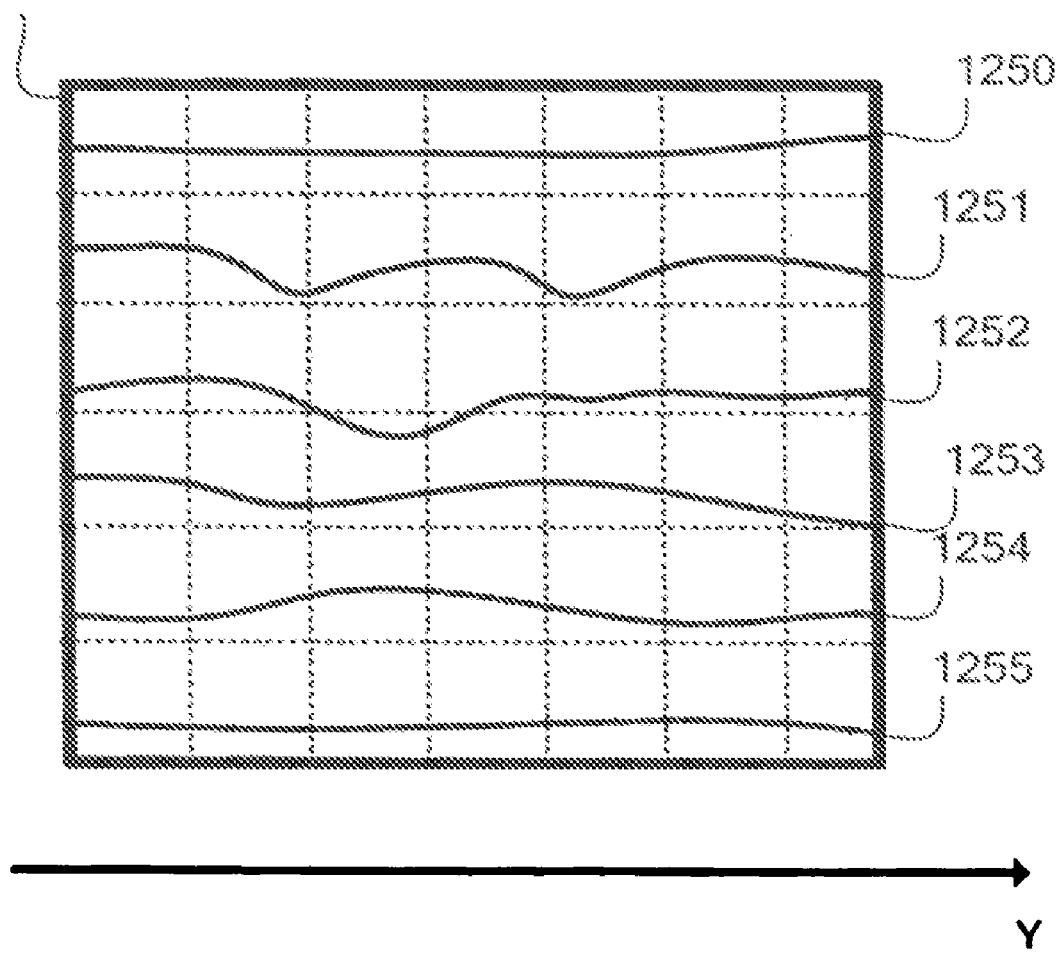
FIG. 12 illustrates a reflection of the light pattern of FIG. 10 as detected by image capture instrument.

FIG. 11 illustrates the scanned pattern of light 1148 projected on the object 1180 to be imaged. FIG. 12 illustrates the light pattern reflected from the object 1180 as incident to the image sensor 1234. For the observed projected curves 1250-1255 on the object, each curve corresponds to one of the curves 1150-1155 shown in FIG. 11 and a corresponding one of the curves 1050-1055 shown FIG. 10. Accordingly, for each curve 1250-1255, the corresponding relations $\theta(y)$, $z_{base}(y)$ and $x_{base}(y)$ may be selected that were pre-computed during a calibration. For each point ($x_{observed}$, $y_{observed}$) on each curve 1250-1255, $$\Delta x = x_{observed} - x_{base}(y_{observed}) \tag{3}$$

Equation (2) may be used to determine $\Delta z$ using $\theta(y_{observed})$, and consequently $$z_{observed} = \Delta z + z_{base}(y_{observed}) \tag{4}$$

The collection of points ($x_{observed}, y_{observed}, z_{observed}$) obtained, form a 3D image of the object 1180.

A maximum displacement for a curve may be determined by:

$$\Delta x = (d_1 - d_2) \text{Tan } \theta \tag{4}$$

A maximum number $n_{max}$ of simultaneously distinguishable curves 1050 may be determined according to $n_{max} = X_{max}/\Delta x$ or equivalently $$n_{max} = \frac{X_{max}}{(d_1 - d_2)\text{Tan}\theta_{max}} \tag{5}$$

The number $n_{max}$ increases with a decreasing depth of field $d_1 - d_2$ and increases with a smaller $\theta_{max}$. The accuracy of the determination also may decrease with smaller $\theta_{max}$ values.

Where the number of curves n exceeds $n_{max}$, any ambiguity in the labeling of the lines may be resolved by associating the observed curves into groups of adjacent curves. For each group of adjacent curves, if at least one curve is correctly labeled, then all other curves in that group may be labeled using adjacency. A method to determine the correct labeling of at least one curve in a group may include considering a second pattern where the number of curves is less than $n_{max}$ and may be at an angle relative to the first pattern. The curves of the second pattern may be properly labeled, and intersections of the curves of the second pattern with the curves of the first pattern may be used to deduce labeling of some subset of the curves in the first pattern. This may be repeated with additional patterns until all curves are correctly labeled.

Figure 13:
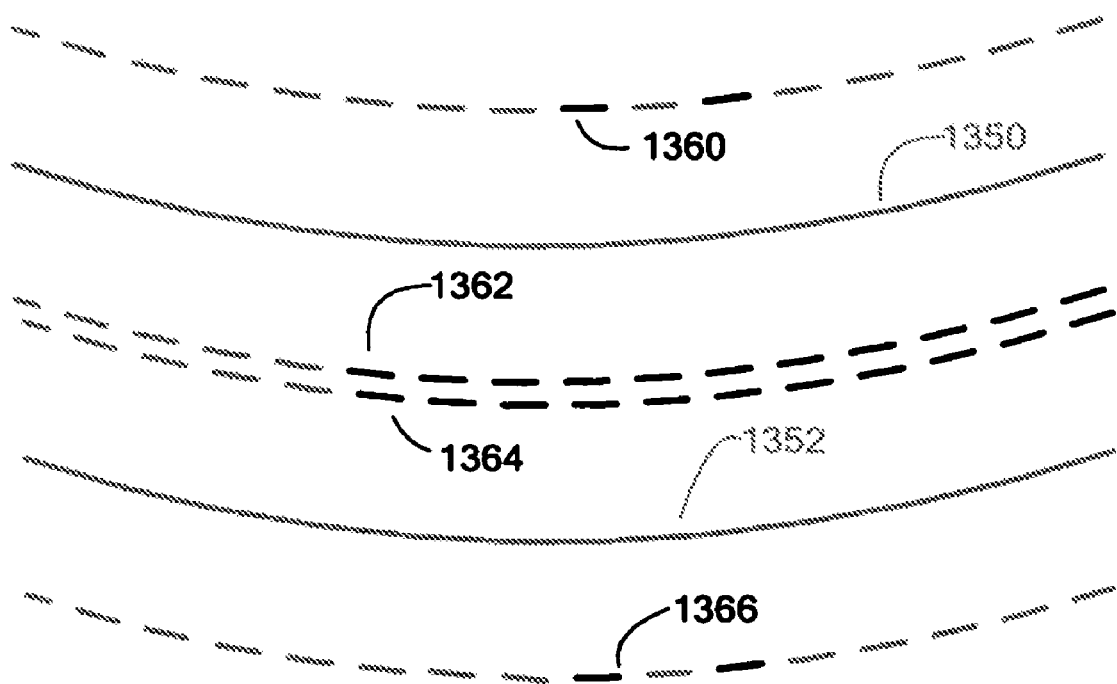
FIG. 13 illustrates multiple laser profiles projected towards an object.

FIG. 13 illustrates scanned lines 1350-1352 on the surface of an object. The scanned line 1350 has associated with it a region bounded by the boundary curves 1360 and 1362. The region bounded by boundary lines 1360 and 1362 is determined by a pre-scan event or calibration data, so that the scanned line 1350 may be identified separately from other scanned lines, such as an adjacent line 1352. Adjacent line 1352 is associated with it its own region bounded by 1364 and 1366. Multiple scanned lines may be projected simultaneously, where each scanned line is uniquely identified, even when projected onto a surface that is not substantially flat.

Figure 14:
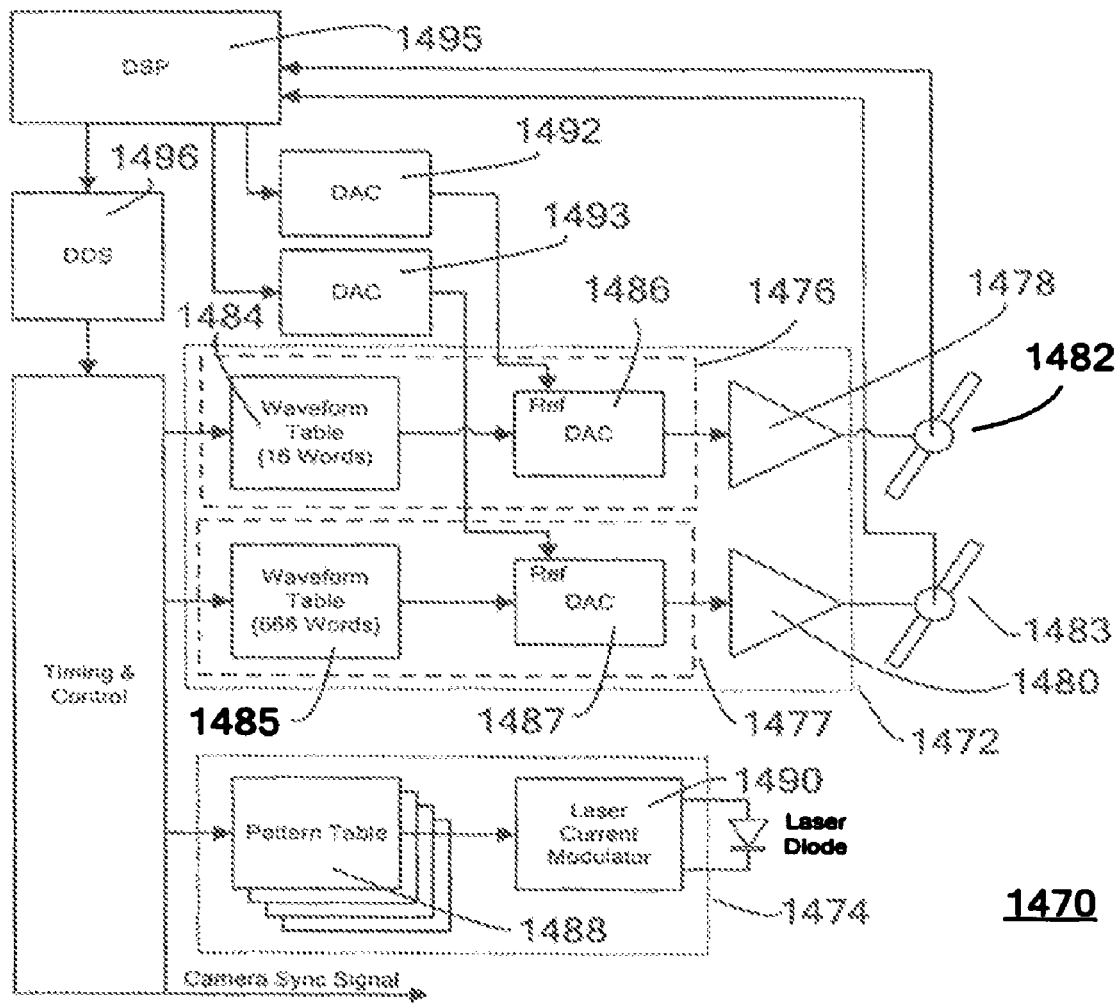
FIG. 14 illustrates an electronic circuit that for controlling the generation of a line pattern.

FIG. 14 illustrates an example of a pattern-projection system 1470. The pattern-projection system 1470 may be incorporated with, part of or a component of the electrical circuit 112. The pattern-projection system 1470 includes a scanner mirror driver circuit 1472 and a laser driver circuit 1474. The mirror driver circuit 1472 includes a RAM-based arbitrary waveform generator (AWG) 1476, 1477 and a transconductance power amplifier stage 1478, 1480 corresponding to a scanner 1482, 1483.

The AWG 1476 corresponding to a high speed scanner 1482 includes a 16-entry waveform table 1484 and a 12-bit digital-to-analog converter (DAC) 1486. The waveform table 1484 may be incremented at approximately 320 KHz to produce a sinusoidal waveform of approximately 20 KHz.

The AWG 1477 corresponding to a low-speed scanner 1483 includes a 666-entry waveform table 1485 and a 12-bit DAC 1487. The waveform table 1485 is incremented once per high-speed mirror cycle to produce a sinusoidal waveform of approximately 30 Hz. The two AWGs 1476, 1477 create a repeating raster pattern at approximately 30 frames per second. Electrical signals synchronize a camera system to the scanner driver. A reference input to each DAC 1486, 1487 is driven by a variable voltage 1492, 1493 to dynamically adjust the horizontal and vertical dimensions of the raster.

The high-speed scanner 1482 is driven at a resonance frequency in the range of about 20 KHz. A position feedback signal of the scanner 1482 may be used with a closed-loop control using a DSP 1495 and a DDS 1496 to adjust drive frequency of the drive signal to track variation in the resonance frequency. The frame rate of the raster pattern may change with the high-speed resonance frequency of the scanner 1482. An example of the DSP includes model number TMS320LF2407A by Texas Instruments. An example of the DDS includes model number AD9834 by Analog Devices.

The laser driver circuit 1470 may include a multiple-bank random access memory (RAM)-based pattern table 1488 and a laser diode current modulator 1490. The RAM-based pattern table 1488 includes multiple banks of memory, where each bank includes a bit-mapped pixel image to be displayed during a single-pattern frame. A counter synchronized with the raster of the scanner raster generator accesses the pattern table 1488 and to present the pixel data to the laser diode current modulator 1490 to produce a repeating pattern. Each bank of the pattern table 1488 may be loaded with a discrete pattern. Multiple single-pattern frames may be combined into repeating multiple-frame sequences with linked-list mechanism.

Figure 15:
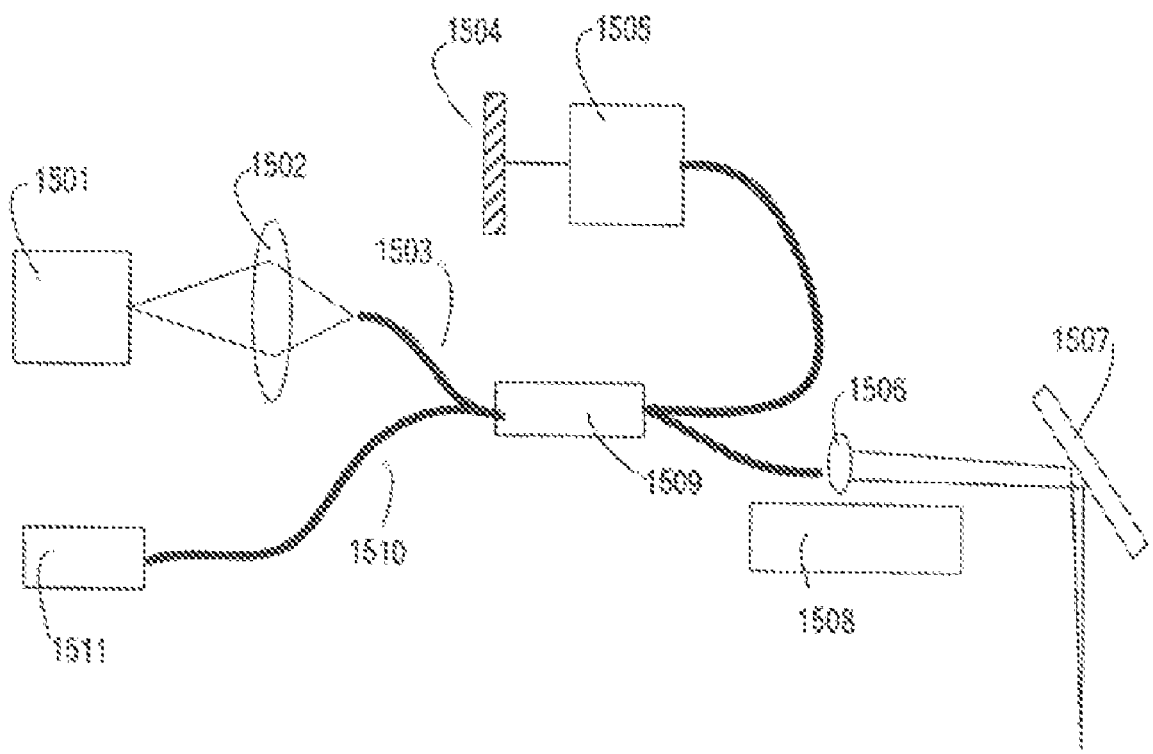
FIG. 15 illustrates an intra-oral digitizer with a low coherence light source coupled to the scanning system and a coupler to a reference beam on an optical delay line.

FIG. 15 illustrates a laser digitizer 1500 configured as an optical coherence tomography ("OCT") or confocal sensor. The laser digitizer includes a fiber-coupled laser 1511. The laser source 1511 may be a low coherence light source coupled to a fiber optic cable 1510, coupler 1509 and detector 1501. The coupler, an optical delay line 1505 and reflector 1504 return delayed light to the coupler 1509. The coupler 1509 splits the light from the light source into two paths. The first path leads to the imaging optics 1506, which focuses the beam onto a scanner 1507, which steers the light to the surface of the object. The second path of light from the light source 1511 via the coupler 1509 is coupled to the optical delay line 1505 and to the reflector 1504. This second path of light is of a controlled and known path length, as configured by the parameters of the optical delay line 1505. This second path of light is the reference path. Light is reflected from the surface of the object and returned via the scanner 1507 and combined by the coupler 1509 with the reference path light from the optical delay line 1505. This combined light is coupled to an imaging system 1501 and imaging optics 1502 via a fiber optic cable 1503. By utilizing a low coherence light source and varying the reference path by a known variation, the laser digitizer provides an Optical Coherence Tomography (OCT) sensor or a Low Coherence Reflectometry sensor. The focusing optics 1506 may be placed on a positioning device 1508 in order to alter the focusing position of the laser beam and to operate as a confocal sensor.

Although embodiments of the invention are described in detail, it should be understood that various changes, substitutions and alterations can be made hereto without departing from the spirit and scope of the invention as described by the appended claims. The laser source may include a laser or LED, and the collimating optics may include optics that circularize the generally elliptical beam-produced by such sources. This system may produce a circular spot on the object to provide a generally uniform line when the beam scanned across the object.

The light source may positioned proximate to the intra-oral laser digitizer remotely through a light guide such as optical fiber. The light source may be remote from the sensor structure and to provide for an intra-oral device having smaller dimensions.

A second light source 129 (LED, incandescent bulb, laser, or other) may provide a background light so that the intra-oral laser digitizer may be used as a standard 2D dental camera. This second light source may be located at or near the imaging optical path. The second light source also may be placed remote to the sensor structure with the light brought to the optical path through a light guide.

The intra-oral system also may include a one- or two-axis tilt sensor. The computer may monitor the angles of the tilt sensor, and the received images of the scanned lines to determine a profile for the object. A one-, two- or three-axis accelerometer may determine approximate position changes of the intra-oral digitizer in one, two or three axes.

The system also may include a laser light source having a high speed modulation system. The modulation system switches the laser on and off at a high rate (typically several MHz), reducing the coherence of the laser source and degree of speckle produced by the laser source on the object.

The scanning system may include a single mirror that scans in two orthogonal axes or other non-parallel arrangement. An example of such a micro-mirror scanner is the bi-axial MEMS scanner of Microvision of Washington. The scanning system may include two mirrors that scan in two orthogonal directions or other non-parallel arrangement.

The imaging sensor may be CMOS sensor or a CCD sensor that captures images at high speeds. A processor processes captured images, such that if the probe moves relative to the object, the software adjusts the captured data so that an accurate digitization occurs. The imaging system may include a small image sensor and objective lens mounted directly at the end of the sensor probe to provide a smaller intra-oral probe through elimination of the relay lenses.

The laser source may include a laser source and line generating optics. This laser source produces one or more lines directed to a one axis laser scanner to provide for a low speed scanner or no scanner based on the line generating optics producing sufficient number of separate line segments.

The imaging system may include an objective, relay lens, asymmetric lens system, and a linear sensor array. A linear sensor array or analog position sensor may be read for each pixel position. The asymmetric lens images the scanning field onto the line detector. The triangulation angle causes the laser spot to be imaged onto different elements of the line detector as the object height changes, allowing fast scanning of the object.

A series of imaged laser segments on the object from a single sample position interlace between two or multiple 3D maps of the sample from essentially the same sample position. The time period to measure each interlaced 3D map is reduced to a short interval and relative motion effects between the intra-oral device and the patient are reduced. The interlaced 3D maps may be aligned with software to produce an effective single view dense 3D point cloud that has no motion induced inaccuracies or artifacts. For example, in a 10 step interlacing scheme, each image may be captured in $\frac{1}{30}^{th}$ of a second. When scanning over 0.3 seconds, the present invention reduces affects of operator motion. The motion of the operator between each subframe may be tracked mathematically through reference points in the dataset itself. The operator motion is removed in subsequent analysis, allowing a system with a framerate significantly lower than would otherwise be required.

Multiple dense 3D point clouds also may be acquired from approximately the same position, and mathematically aligned (i.e., moved relative to each other to minimize the distance between them so as to cause related features in each to become superimposed), and statistical methods used to further improve the accuracy of the data (for example, Gaussian filtering).

A low resolution pre-scan of the surface determines approximate geometry. Referring to this pre-scan, an approximate envelope of subsequent laser lines is determined by performing inverse calculation of a laser line centroid to 3D coordinate. Since these envelopes are not rectangular and combined with the assumption that the surface does not change dramatically locally one can greatly increase the number of simultaneous lines projected on the surface and identifiable in the image, increasing the effective scanning rate. In and example of N lines being scanned simultaneously with a system capable of processing F frames per second, an effective F*N frames per second processing rate, or multiplied by a factor of N, may be achieved.

The imaging system may be located remotely from the imaging sensor. Through relay optics such as a coherent fiber imaging bundle, the scanning system may be located remotely from the imaging sensor. The Fourier transform of the object image is transferred through the fiber imaging bundle. By transferring the Fourier transform through the fiber bundle, more of the high frequency components of the object image remain. Also, the effects of the fiber bundle can be removed by removing the frequency components from the Fourier transformed image, which corresponds to the fiber bundle.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

The invention claimed is:

1. An intra-oral laser digitizer system comprising:
a first light source having collimating optics configured to generate a collimated beam of light;
a scanner optically coupled to the first light source and configured to scan the collimated beam along at least two axes to generate a pattern;
an optics relay coupled to the scanner and configured to relay the pattern towards a remote object to be imaged;
an image optics system having an optical axis configured to detect a reflection of the pattern from the remote object at an angle θ with respect to the optics relay and to generate data representative of a surface of the object based on the reflection of the pattern, wherein the image optics system comprises an image sensor, a reflecting surface configured to capture a reflection of the pattern, and an optics relay coupled to the reflecting surface and configured to relay the reflection of the pattern from the reflecting surface to the image sensor;
a processor coupled to the scanner and the image optics system configured to generate a three-dimensional image of the object based on the data; and
a second light source located adjacent the optical axis to provide a background light.

2. The intra-oral laser digitizer of claim 1 where the remote object comprises any one of: an in vivo dental item, a dental preparation, a dental model, a dental mold, or a dental casting.

3. The intra-oral laser digitizer of claim 1 where the first light source comprises a low coherence light source.

4. The intra-oral laser digitizer as described in claim 1 wherein the optics relay coupled to the reflecting surface is co-linear to the optics relay coupled to the scanner.

5. An intra-oral laser digitizer, comprising:
a first light source having collimating optics configured to generate a collimated beam of light;
a scanner optically coupled to the light source and configured to scan the collimated beam along at least two axes to generate a pattern comprising a set of segments;
a first optics relay coupled to the scanner and configured to relay the pattern towards a remote object to be imaged;
a reflecting surface configured to capture a reflection of the pattern from the object at an angle θ with respect to the first optics relay;
a second optics relay, co-linear to the first optics relay, the second optics relay coupled to the reflecting surface and configured to relay the reflection of the pattern toward an image sensor; and
second light source that provides a background light.

6. The intra-oral laser digitizer as described in claim 5 wherein the image sensor generates a first data set representative of a surface of the object based on the reflection of the pattern.

7. The intra-oral laser digitizer as described in claim 6 wherein the scanner generates a second pattern comprising a set of segments, and wherein the image sensor generates a second data set representative of a surface of the object based on a reflection of the second pattern.

8. The intra-oral laser digitizer as described in claim 7 further including a processor, under program control, to generate a three-dimensional image of the object based on the first and second data sets.

9. The intra-oral laser digitizer as described in claim 8 wherein the processor generates a representation of the object based on the reflection of the pattern as detected by the image sensor.

10. An intra-oral laser digitizer system comprising:
a first laser light source having collimating optics configured to generate a collimated beam of light;
a scanner optically coupled to the first light source and configured to scan the collimated beam through a curvilinear path along at least two axes to generate a pattern;
a first optics relay coupled to the scanner and configured to relay the pattern towards a dental object to be imaged;

an image optics system having an optical axis configured to detect a reflection of the pattern from the dental object at an angle θ with respect to the first optics relay and to generate data representative of a surface of the dental object based on the reflection of the pattern, wherein the image optics system comprises an image sensor, a reflecting surface configured to capture the reflection of the pattern, and a second optics relay coupled to the reflecting surface and configured to relay the reflection of the pattern from the reflecting surface to the image sensor;

a processor coupled to the scanner and the image optics system, the processor configured to generate a three-dimensional image of the dental object based on data representative of the reflection of the pattern; and a second light source located adjacent the optical axis to provide a background light.

11. The intra-oral laser digitizer of claim 10 wherein the dental object comprises at least one of: an in vivo dental item, a dental preparation, a dental model, a dental mold, or a dental casting.

12. The intra-oral laser digitizer of claim 10 wherein the first light source comprises a low coherence laser light source.

13. The intra-oral laser digitizer as described in claim 10 wherein the first optics relay coupled to the reflecting surface is co-linear to the second optics relay coupled to the scanner.

14. The intra-oral laser digitizer as described in claim 10 wherein the image sensor generates the data representative of the reflection of the pattern.

* * * * *